United States Patent
Yano et al.

(10) Patent No.: US 10,867,019 B2
(45) Date of Patent: Dec. 15, 2020

(54) PERSONAL AUTHENTICATION DEVICE, PERSONAL AUTHENTICATION METHOD, AND PERSONAL AUTHENTICATION PROGRAM USING ACOUSTIC SIGNAL PROPAGATION

(71) Applicants: NEC Corporation, Tokyo (JP); Shouhei Yano, Nagaoka (JP)

(72) Inventors: Shouhei Yano, Nagaoka (JP); Takayuki Arakawa, Tokyo (JP); Takafumi Koshinaka, Tokyo (JP); Hitoshi Imaoka, Tokyo (JP); Hideki Irisawa, Tokyo (JP)

(73) Assignees: NEC CORPORATION, Tokyo (JP); Shouhei Yano, Nagaoka (JP)

( * ) Notice: Subject to any disclaimer, the term of this patent is extended or adjusted under 35 U.S.C. 154(b) by 0 days.

(21) Appl. No.: 15/769,967

(22) PCT Filed: Oct. 18, 2016

(86) PCT No.: PCT/JP2016/080833
§ 371 (c)(1),
(2) Date: Apr. 20, 2018

(87) PCT Pub. No.: WO2017/069118
PCT Pub. Date: Apr. 27, 2017

(65) Prior Publication Data
US 2018/0307818 A1    Oct. 25, 2018

(30) Foreign Application Priority Data
Oct. 21, 2015    (JP) .................................. 2015-206857

(51) Int. Cl.
*G06F 21/32*    (2013.01)
*G10L 25/51*    (2013.01)
(Continued)

(52) U.S. Cl.
CPC .............. *G06F 21/32* (2013.01); *A61B 5/117* (2013.01); *A61B 5/12* (2013.01); *A61B 5/6817* (2013.01);
(Continued)

(58) Field of Classification Search
CPC .................................. G10L 17/02; G06F 21/32
(Continued)

(56) References Cited

U.S. PATENT DOCUMENTS

| | | | | |
|---|---|---|---|---|
| 5,787,187 A | * | 7/1998 | Bouchard ................ | A61B 5/12 382/115 |
| 6,231,521 B1 | * | 5/2001 | Zoth ...................... | A61B 5/121 128/898 |

(Continued)

FOREIGN PATENT DOCUMENTS

| | | |
|---|---|---|
| JP | 2003-058190 A | 2/2003 |
| JP | 2004-065363 A | 3/2004 |

(Continued)

OTHER PUBLICATIONS

Akio Ando "Real-time Voice Recognition System", Institute of Electronics, Information and Communication Engineers, 2003, p. 28-30.
International Search Report of PCT/JP2016/080833 dated Jan. 10, 2017 [PCT/ISA/210].

*Primary Examiner* — Shaun Roberts
(74) *Attorney, Agent, or Firm* — Sughrue Mion, PLLC

(57) ABSTRACT

A personal authentication device includes: acoustic signal transmission means 701 for transmitting a first acoustic signal to a part of a head of a user; acoustic signal observation means 702 for observing a second acoustic signal which is an acoustic signal after the first acoustic signal propagates through the part of the head; acoustic property calculation means 703 for calculating an acoustic property from the first acoustic signal and the second acoustic signal;
(Continued)

and user identification means 704 for identifying the user, based on the acoustic property or a feature value extracted from the acoustic property and relating to the user.

11 Claims, 11 Drawing Sheets

(51) Int. Cl.
*G01N 29/11* (2006.01)
*G01N 29/46* (2006.01)
*A61B 5/117* (2016.01)
*A61B 5/12* (2006.01)
*A61B 5/00* (2006.01)
*G10L 17/02* (2013.01)
*G10L 21/0208* (2013.01)

(52) U.S. Cl.
CPC ............ *G01N 29/11* (2013.01); *G01N 29/46* (2013.01); *G10L 17/02* (2013.01); *G10L 21/0208* (2013.01); *G10L 25/51* (2013.01); *G01N 2291/015* (2013.01); *G01N 2291/044* (2013.01); *G01N 2291/102* (2013.01)

(58) Field of Classification Search
USPC .......................................................... 704/246
See application file for complete search history.

(56) References Cited

U.S. PATENT DOCUMENTS

| | | | | |
|---|---|---|---|---|
| 2005/0063552 A1* | 3/2005 | Shuttleworth | ........... | H03G 3/32 381/57 |
| 2006/0265218 A1* | 11/2006 | Samadani | ........... | G10L 21/0208 704/233 |
| 2007/0086596 A1* | 4/2007 | Kino | ........... | H04S 7/301 381/59 |
| 2007/0156063 A1* | 7/2007 | Zoth | ........... | A61B 5/121 600/559 |
| 2008/0273709 A1* | 11/2008 | Thiagarajan | ........... | A61B 7/04 381/67 |
| 2010/0328033 A1* | 12/2010 | Kamei | ........... | A61B 8/0875 340/5.82 |
| 2013/0163781 A1* | 6/2013 | Thyssen | ........... | H04R 3/007 381/94.3 |
| 2015/0341717 A1* | 11/2015 | Song | ........... | H04R 1/08 381/110 |
| 2016/0035337 A1* | 2/2016 | Aggarwal | ........... | H03G 3/20 381/94.2 |

FOREIGN PATENT DOCUMENTS

| | | | |
|---|---|---|---|
| JP | 2007-116373 | A | 5/2007 |
| JP | 2010-086328 | A | 4/2010 |
| JP | 2010-286702 | A | 12/2010 |
| WO | 2009/104437 | A1 | 8/2009 |

\* cited by examiner

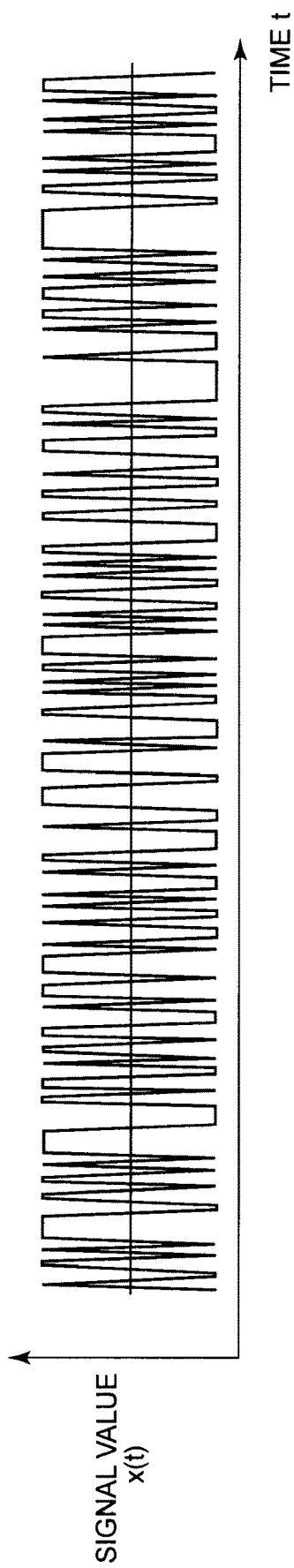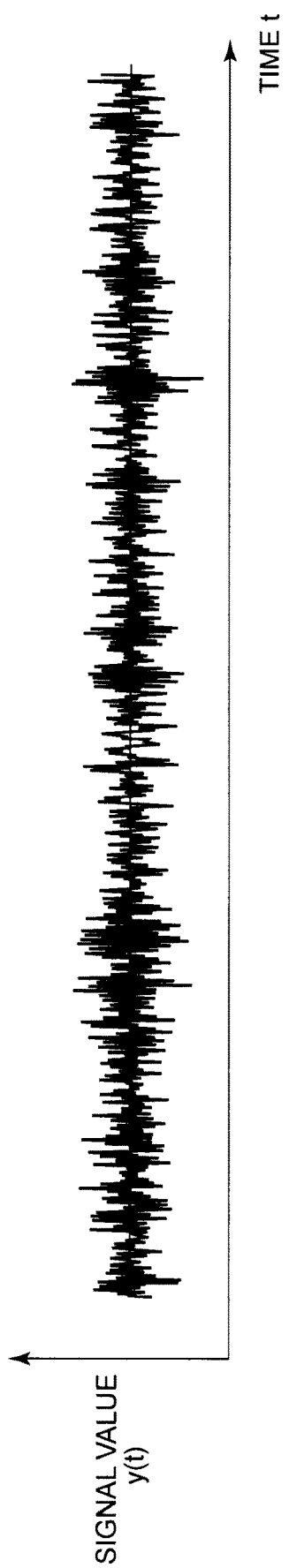

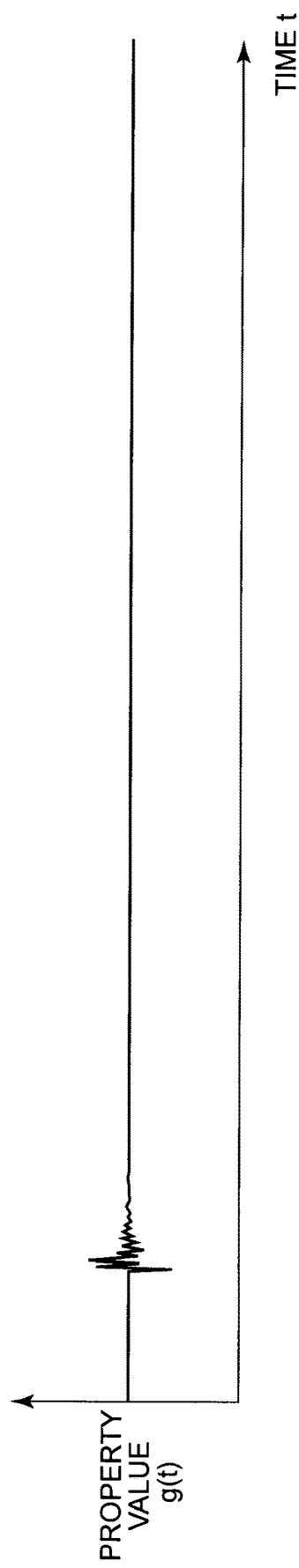

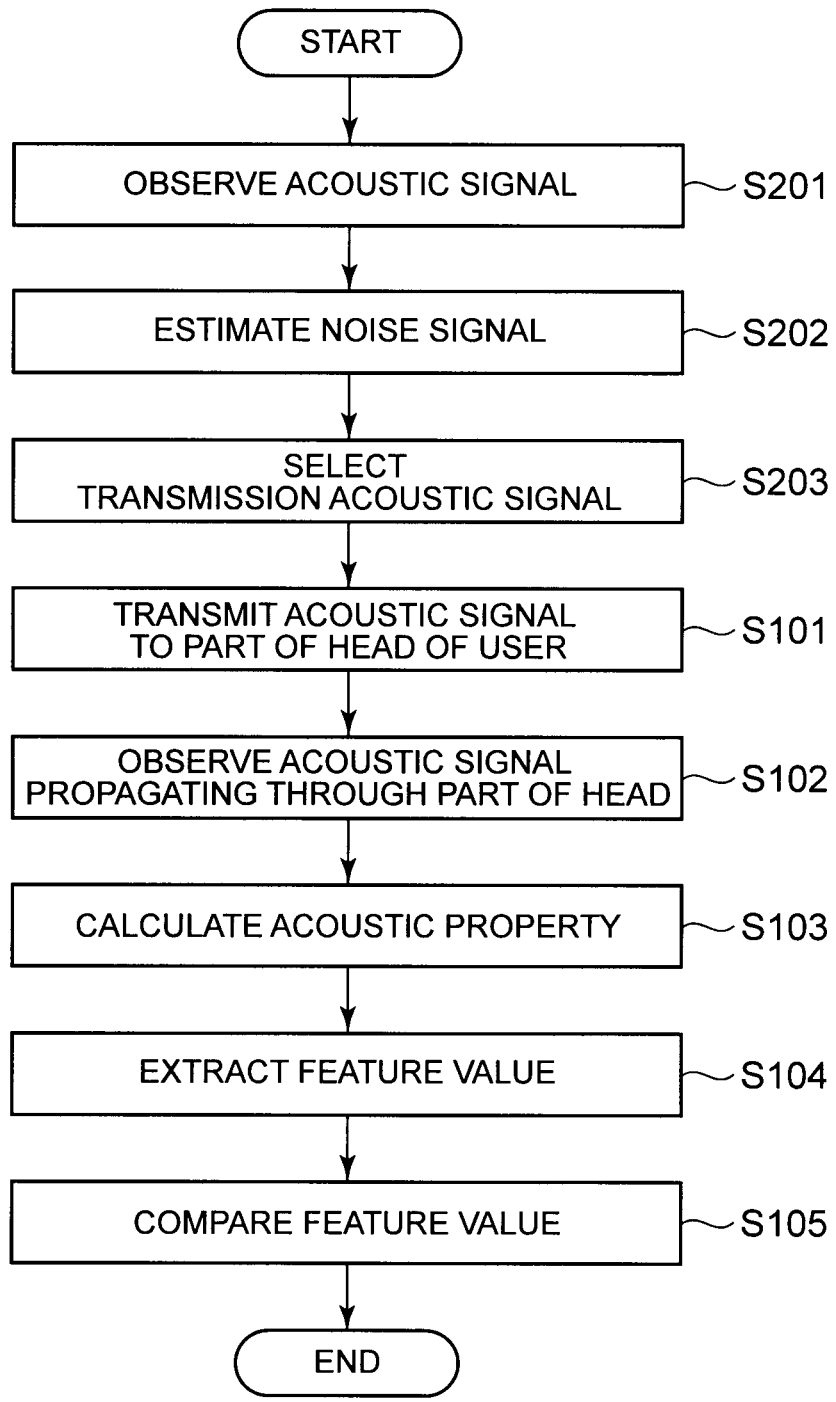

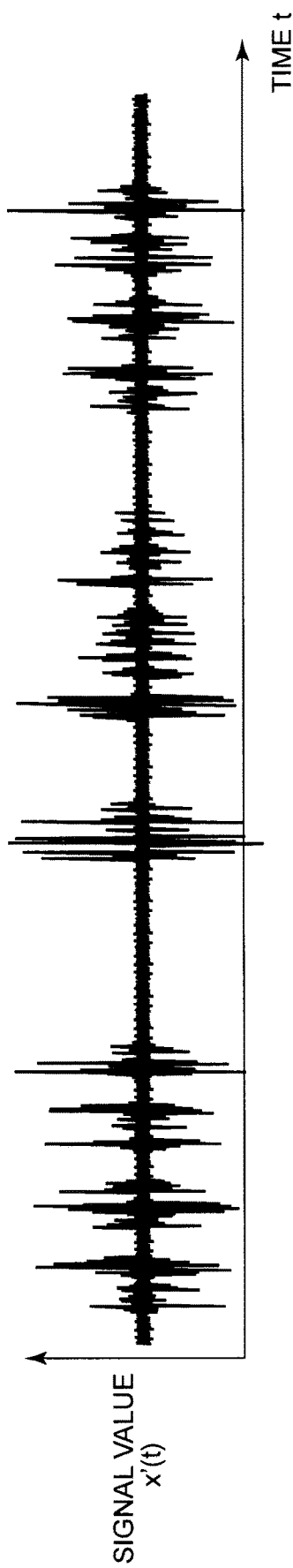

PERSONAL AUTHENTICATION DEVICE, PERSONAL AUTHENTICATION METHOD, AND PERSONAL AUTHENTICATION PROGRAM USING ACOUSTIC SIGNAL PROPAGATION

CROSS REFERENCE TO RELATED APPLICATIONS

This application is a National Stage of International Application No. PCT/JP2016/080833, filed Oct. 18, 2016, claiming priority based on Japanese Patent Application No. 2015-206857, filed Oct. 21, 2015, the contents of all of which are incorporated herein by reference in their entirety.

TECHNICAL FIELD

The present invention relates to a personal authentication device, a personal authentication method, and a personal authentication program for authenticating a person.

BACKGROUND ART

Personal authentication based on biological individual differences (biometrics-based authentication) has low risk of leakage or theft, as compared with passwords and the like. Accordingly, personal authentication based on biological individual differences has been increasingly introduced for the purpose of specifying persons and verifying their rights and for the purpose of security protection. Conventionally known personal authentication technologies based on biological individual differences use fingerprint, vein, face, iris, voice, and the like, as biometric information. Of these, personal authentication using voice can be performed with not a special device but an inexpensive general-purpose device such as a telephone or a microphone.

Patent Literature (PTL) 1 discloses, as an example of personal authentication using voice, a method of converting voice data to be authenticated into a feature value, measuring its similarity to a preregistered user's feature value, and performing authentication based on the result.

PTL 2 discloses a method of performing personal authentication using bone conducted sound received by a bone conduction microphone, instead of voice propagating through air.

CITATION LIST

Patent Literatures

PTL 1: Japanese Patent Application Laid-Open No. 2010-286702
PTL 2: Japanese Patent Application Laid-Open No. 2003-58190

Non Patent Literature

NPL 1: Akio Ando "Real-time Voice Recognition System", Institute of Electronics, Information and Communication Engineers, 2003, p. 28-30

SUMMARY OF INVENTION

Technical Problem

A problem lies in that, with a method of acquiring biometric information and performing personal authentication, the user needs to perform some kind of action for authentication. For example, in the case of personal authentication using fingerprint or vein, the user's action such as placing his or her finger on a dedicated scanner is necessary. In the case of personal authentication using face or iris, the user's action such as facing a camera is necessary. In the case of personal authentication using voice or bone conducted sound, the user's action such as uttering a password is necessary. The user required to perform such action has a psychological and/or physical burden.

In view of the problem stated above, the present invention has an object of providing a personal authentication device, a personal authentication method, and a personal authentication program that lessen a psychological and/or physical burden on a user to be authenticated.

Solution to Problem

A personal authentication device according to the present invention includes: acoustic signal transmission means for transmitting a first acoustic signal to a part of a head of a user; acoustic signal observation means for observing a second acoustic signal which is an acoustic signal after the first acoustic signal propagates through the part of the head; acoustic property calculation means for calculating an acoustic property from the first acoustic signal and the second acoustic signal; and user identification means for identifying the user, based on the acoustic property or a feature value extracted from the acoustic property and relating to the user.

A personal authentication method according to the present invention includes: transmitting a first acoustic signal to a part of a head of a user; observing a second acoustic signal which is an acoustic signal after the first acoustic signal propagates through the part of the head; calculating an acoustic property from the first acoustic signal and the second acoustic signal; and identifying the user, based on the acoustic property or a feature value extracted from the acoustic property and relating to the user.

A personal authentication program according to the present invention causes a computer to execute: a process of calculating an acoustic property, from a first acoustic signal transmitted to a part of a head of a user and a second acoustic signal which is an acoustic signal after the first acoustic signal propagates through the part of the head; and a process of identifying the user, based on the acoustic property or a feature value extracted from the acoustic property and relating to the user.

Advantageous Effects of Invention

According to the present invention, it is possible to provide personal authentication that lessens a psychological and/or physical burden on a user to be authenticated.

BRIEF DESCRIPTION OF DRAWINGS

FIGS. 4(a) and 4(b) are graphs depicting an example of a transmission acoustic signal and an observation acoustic signal.

FIG. 5 is a graph depicting an example of an impulse response as acoustic property.

FIG. 11 is a flowchart depicting an example of the operation of the personal authentication device in Exemplary Embodiment 4.

FIGS. 12(a) and 12(b) are explanatory diagrams depicting an example of superimposing, on musical sound, another acoustic signal.

DESCRIPTION OF EMBODIMENT

Exemplary Embodiment 1

Figure 1:
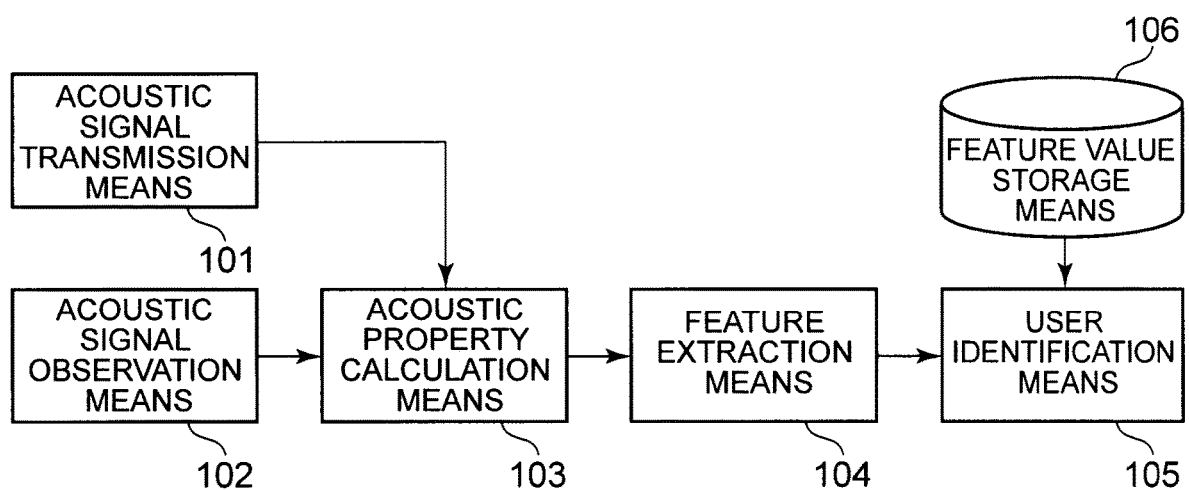
FIG. 1 is a block diagram depicting an example of the structure of a personal authentication device in Exemplary Embodiment 1.

Exemplary embodiments of the present invention are described below, with reference to drawings. FIG. 1 is a block diagram depicting an example of the structure of a personal authentication device in Exemplary Embodiment 1. The personal authentication device depicted in FIG. 1 includes acoustic signal transmission means 101, acoustic signal observation means 102, acoustic property calculation means 103, feature extraction means 104, user identification means 105, and feature value storage means 106.

The acoustic signal transmission means 101 transmits an acoustic signal to a part of the head of a first user. The part of the head to which the acoustic signal is transmitted is a region where a cavity is formed in the head, and may be at least a part of a region to which an accessory or a device for producing an acoustic effect can be attached or brought close.

The acoustic signal observation means 102 observes an acoustic signal after the acoustic signal transmitted from the acoustic signal transmission means 101 propagates through the part of the head of the first user. More specifically, the part of the head which is the propagation path of the acoustic signal may be at least a part of the skull, brain, sense organ, and cavity therebetween constituting the head.

The acoustic property calculation means 103 calculates the acoustic property of the acoustic signal propagating through the part of the head of the user, based on the acoustic signal transmitted from the acoustic signal transmission means 101 and the acoustic signal observed by the acoustic signal observation means 102.

The feature extraction means 104 calculates a feature value relating to the user in which the acoustic signal has propagated, from the calculated acoustic property.

The feature value storage means 106 stores an extracted feature value for at least one predetermined user beforehand. Each user for which a feature value is stored in the feature value storage means 106 is hereafter also referred to as "registered user". For example, the feature value storage means 106 may store beforehand, for each of a plurality of users, a feature value extracted using a feature value extraction process by the acoustic signal transmission means 101, the acoustic signal observation means 102, the acoustic property calculation means 103, and the feature extraction means 104 or their equivalent structure.

The user identification means 105 compares the feature value obtained by the feature extraction means 104 with the feature value of the registered user stored in the feature value storage means 106, to determine whether or not the first user corresponds to the registered user.

Figure 2:
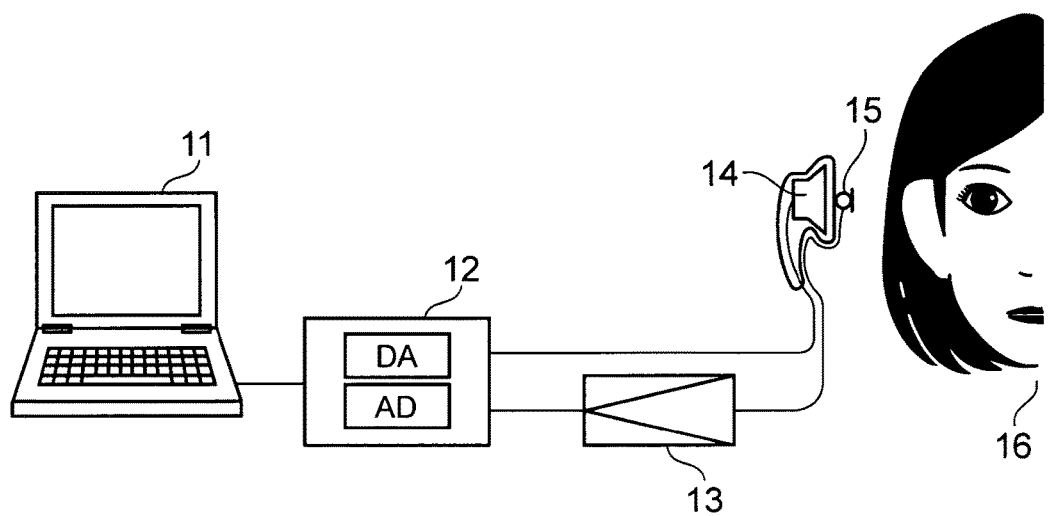
FIG. 2 is a schematic diagram depicting an example of the specific structure of the personal authentication device in Exemplary Embodiment 1.

FIG. 2 is a schematic diagram depicting an example of the specific structure of the personal authentication device in this exemplary embodiment. The personal authentication device depicted in FIG. 2 includes a personal computer (PC) 11, a sound processor 12, a microphone amplifier 13, an earphone 14, and a microphone 15. Reference sign 16 is the user (subject) to be authenticated.

The earphone 14 corresponds to the above-mentioned acoustic signal transmission means 101. The microphone 15 corresponds to the above-mentioned acoustic signal observation means 102. The microphone 15 and the earphone 14 are desirably integrated so that their relative positional relationship is unchanged, as depicted in FIG. 2. The present invention is, however, not limited to such, as long as their relative positional relationship is not changed significantly. In FIG. 2, a microphone-integrated earphone that is inserted into the entrance of the ear canal is depicted as an example of the acoustic signal transmission means 101 and the acoustic signal observation means 102. Alternatively, the acoustic signal transmission means 101 and the acoustic signal observation means 102 may be realized by a pinna-covering headphone provided with a microphone (pinna type microphone-integrated earphone). The acoustic signal transmission means 101 and the acoustic signal observation means 102 may be realized by a telephone having a microphone in its receiver portion. In such cases, separate functions may be performed on the right and left sides, e.g. observing, with a microphone located at the entrance of the right ear canal, an acoustic signal transmitted from an earphone located at the entrance of the left ear canal, or vice versa.

The acoustic property calculation means 103, the feature extraction means 104, and the user identification means 105 are each realized by a CPU and memory (both not depicted) included in the PC 11, where the CPU operates according to a program. The feature value storage means 106 is realized by a storage medium (not depicted) such as a hard disk included in the PC 11.

Operation in this exemplary embodiment is described below.

Figure 3:
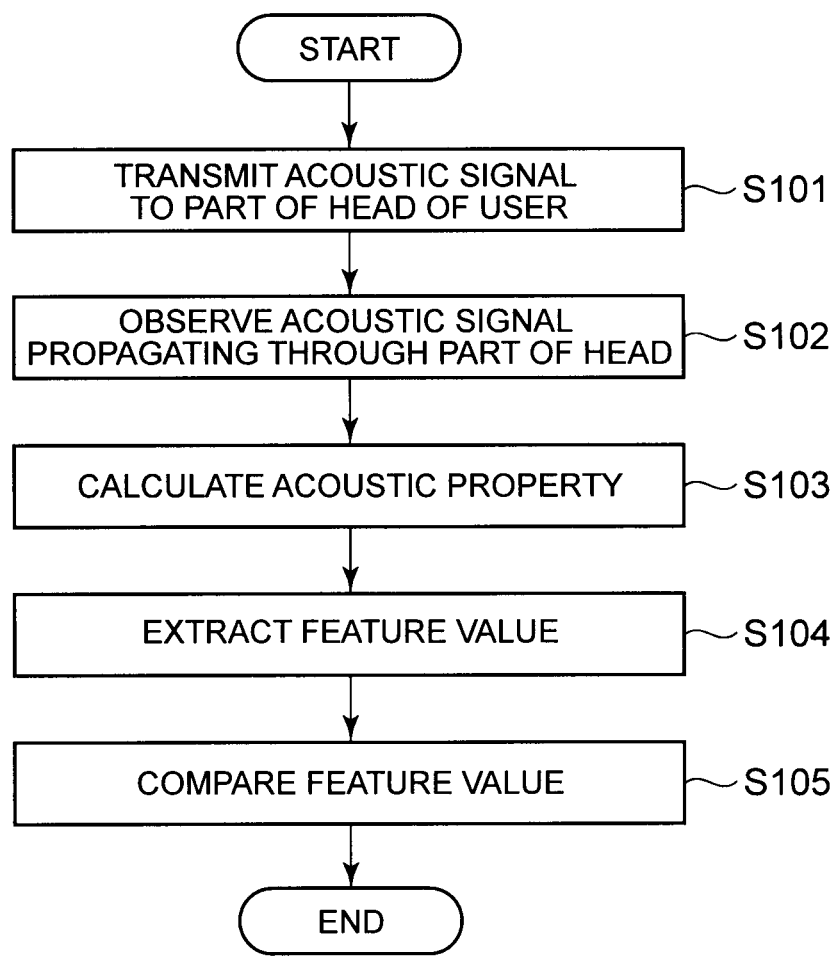
FIG. 3 is a flowchart depicting an example of the operation of the personal authentication device in Exemplary Embodiment 1.

FIG. 3 is a flowchart depicting an example of the operation of the personal authentication device in this exemplary embodiment. In the example depicted in FIG. 3, first the acoustic signal transmission means 101 transmits an acoustic signal to the part of the head of the user to be authenticated (step S101). The acoustic signal transmission means 101 may, for example, transmit the acoustic signal from the entrance of the ear canal into the ear canal. The acoustic signal may be a maximal length sequence (M-sequence) signal, a time stretched pulse (TSP) signal, or the like widely used for the purpose of measuring an impulse response.

FIG. 4(a) is a graph depicting an example of the acoustic signal transmitted by the acoustic signal transmission means 101. In the graph in FIG. 4(a), the horizontal axis represents time t, and the vertical axis represents the signal value x(t) of the acoustic signal transmitted at time t. The acoustic signal transmitted by the acoustic signal transmission means 101 is hereafter also referred to as "transmission acoustic signal".

Subsequently, the acoustic signal observation means 102 observes an acoustic signal after the transmission acoustic signal propagates through the part of the head of the user to be authenticated (step S102).

FIG. 4(b) is a graph depicting an example of the acoustic signal observed by the acoustic signal observation means 102. In the graph in FIG. 4(b), the horizontal axis represents time t, and the vertical axis represents the signal value y(t) of the acoustic signal observed at time t. The acoustic signal observed by the acoustic signal observation means 102 is hereafter also referred to as "observation acoustic signal".

Subsequently, the acoustic property calculation means 103 compares the transmission acoustic signal and the observation acoustic signal, and calculates, from the change between the signals, the acoustic property of the acoustic signal when the acoustic signal propagates through the part of the head of the user (step S103). Examples of the acoustic property include an impulse response, and a transfer function obtained by Fourier transforming or Laplace transforming the impulse response. The acoustic property preferably includes information of how the acoustic signal reflects and/or attenuates in the living body. In the case of placing the earphone and the microphone at the opening of the ear canal and measuring the acoustic property of reflection through the ear canal, the acoustic property may be an ear canal impulse response or an ear canal transfer function.

FIG. 5 is a graph depicting an example of the impulse response as the acoustic property calculated by the acoustic property calculation means 103. In the graph in FIG. 5, the horizontal axis represents time t, and the vertical axis represents the value g(t) of the impulse response of the acoustic signal observed at time t.

The signal value x(t) of the transmission acoustic signal, the signal value y(t) of the observation acoustic signal, and the value g(t) of the impulse response have the relationship defined by the following expression (1).

[Math. 1]

$$y(t) = \int_0^t x(\tau)g(t-\tau)d\tau \quad (1)$$

Values X(f), Y(f), and G(f) respectively obtained by Fourier transforming x(t), y(t), and g(t) have the relationship defined by the following expression (2). Here, f is a frequency band, and G(f) is a transfer function.

$$Y(f) = G(f)X(f) \quad (2)$$

Subsequently, the feature extraction means 104 calculates a feature value from the acoustic property calculated by the acoustic property calculation means 103 (step S104). As the feature value, the impulse response or the transfer function calculated as the acoustic property may be used directly. In detail, the feature extraction means 104 may use, as the feature value, the value of the impulse response at each time or the value of the transfer function at each frequency as the acoustic property. Alternatively, the feature extraction means 104 may calculate a feature value obtained by performing principal component analysis and dimensional compression on the impulse response or the transfer function as the acoustic property, or a mel-frequency cepstrum coefficient (mfcc) described in Non Patent Literature (NPL) 1.

Subsequently, the user identification means 105 compares the feature value obtained by the feature extraction means 104 with the feature value of at least one registered user stored in the feature value storage means 106 beforehand, to determine whether or not the user to be authenticated corresponds to the registered user (step S105). The user identification means 105 may use any of one-to-one authentication and one-to-N authentication as the determination method, where N is an integer of 1 or more.

In the case of using one-to-one authentication, the user identification means 105 compares the feature value of the user to be authenticated (the feature value obtained by the feature extraction means 104) and the feature value of a registered user, on a one-to-one basis. Here, the administrator of the personal authentication device may designate, to the user identification means 105, which registered user is subjected to comparison, using a user ID or the like beforehand. In the case of using one-to-one authentication, for example, the user identification means 105 may calculate the distance between the feature value of the user to be authenticated and the feature value of the designated registered user, and determine that the user and the registered user are the same person in the case where the distance is less than a threshold. The user identification means 105 may determine that the user and the registered user are different persons, in the case where the calculated distance is more than the threshold.

In the case of using one-to-N authentication, the user identification means 105 compares the user to be authenticated and N registered users. The user identification means 105 calculates the distance between the feature value of the user to be authenticated and the feature value of each of the N registered users, and determines that a registered user with the shortest distance is the user to be authenticated. The user identification means 105 may use one-to-one authentication and one-to-N authentication in combination. In this case, the user identification means 105 may perform one-to-N authentication to extract a registered user with the shortest distance, and then perform one-to-one authentication using the extracted registered user for comparison. The calculated distance measure may be, but not limited to, Euclid distance, cosine distance, or the like.

Although the above describes an example where the feature value storage means 106 stores feature values obtained from a plurality of persons beforehand, the feature value storage means 106 may store a statistical model instead of feature values. For example, the statistical model may be a mean and a variance yielded from feature values acquired for each user a plurality of times, or a relational expression calculated using such a mean and variance. The statistical model may be a Gaussian mixture model (GMM) described in PTL 1, a support vector machine (SVM), a model using a neural network, or the like.

As described above, according to this exemplary embodiment, personal authentication is performed based on the characteristics that the acoustic property of an acoustic signal propagating through a part of the head of the user differs between persons. The acoustic property of the propagation through the part of the head of the user is a feature inside the living body unlike a feature observable from outside such as a face or a fingerprint, and therefore has low risk of leakage and is difficult to steal. Moreover, to obtain the acoustic property, two signals, i.e. the transmission acoustic signal and the observation acoustic signal, are necessary. This reduces the risk of acquisition through eavesdropping or the like and forgery, as compared with a method that uses one signal. Furthermore, the only action performed by the user to be authenticated for authentication in this exemplary embodiment is wearing a headphone or an earphone in which a microphone is embedded, or holding a mobile phone or the like with a microphone embedded in its receiver portion over the ear. Thus, according to this exemplary embodiment, the psychological/physical burden of the user can be lessened. For example, by using the personal authentication method in this exemplary embodiment in combination with a voice-based information distribution device such as music distribution, transceiver, and phone call, such personal authentication that puts no additional physical/psychological burden on the user from the original use state can be provided.

In this exemplary embodiment, the acoustic property can be acquired in a relatively short time of about one second. This enables personal authentication to be performed continuously before and after and during service provision. By continuously performing personal authentication using the personal authentication method in this exemplary embodiment, an unauthorized act such as impersonation by another person after authentication can be detected, as compared with the case of performing authentication only the first time or only immediately before some service is provided.

Exemplary Embodiment 2

Figure 6:
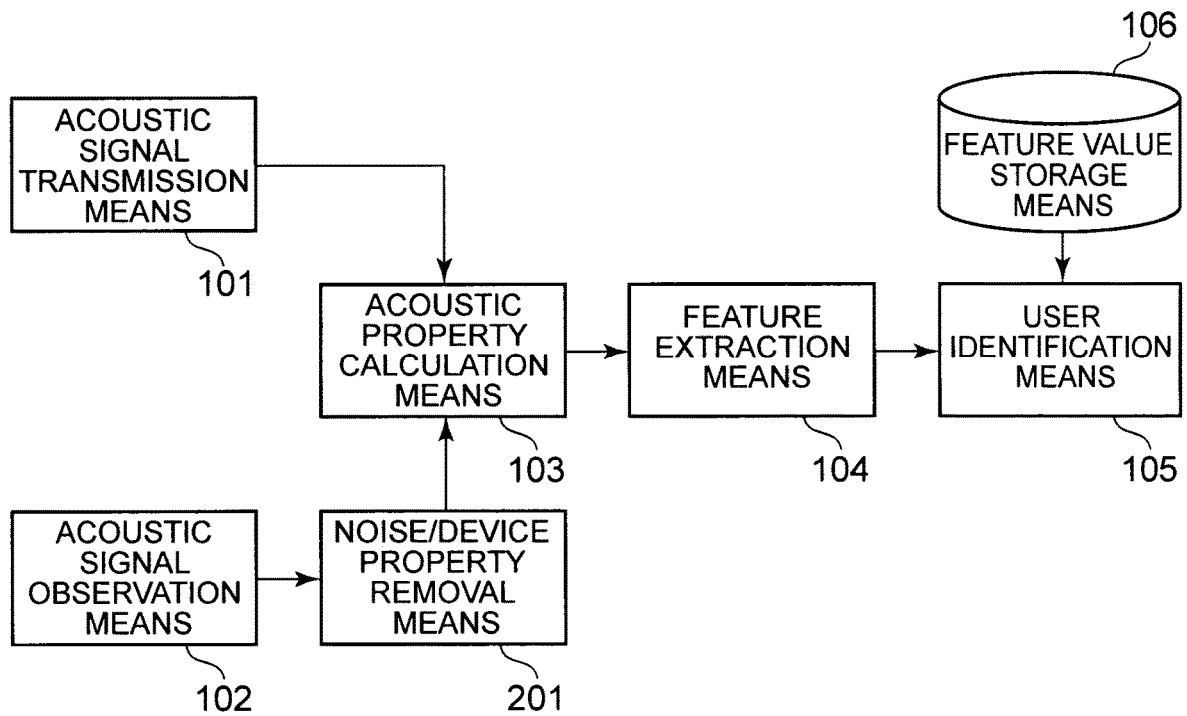
FIG. 6 is a block diagram depicting an example of the structure of a personal authentication device in Exemplary Embodiment 2.

Exemplary Embodiment 2 of the present invention is described below. FIG. 6 is a block diagram depicting an example of the structure of a personal authentication device in Exemplary Embodiment 2 of the present invention. The personal authentication device depicted in FIG. 6 differs from the structure of Exemplary Embodiment 1 depicted in FIG. 1 in that noise/device property removal means 201 is further included.

The observation acoustic signal contains not only acoustic property derived from the user's biometrics, but also various noise such as ambient environmental noise, cardiac sound, respiratory sound, utterance, joint sound, and vibration. Besides, the acoustic signal transmission means 101 and the acoustic signal observation means 102 themselves have acoustic property, which may appear as device property that represents an individual device difference.

In this exemplary embodiment, the noise/device property removal means 201 removes such noise and device property from the observation acoustic signal. With this structure, the acoustic property calculation means 103 can use the observation acoustic signal from which the noise and device property are removed.

A specific method of noise/device property removal is, for example, a method of transmitting the transmission acoustic signal to two locations of the head of the user and observing the respective signals. By performing subtraction on two observation acoustic signals observed from the two locations of the head of the user, it is possible to keep only the biometrics-derived acoustic property dependent on the positional difference between the two locations of the head and remove noise and device property not dependent on the positional difference. The method of observing the acoustic signals at the two locations may be, for example, a method whereby one acoustic signal observation means 102 performs observation twice to obtain two observation acoustic signals, or a method whereby two acoustic signal observation means 102 each perform observation once to obtain two observation acoustic signals. For example, the acoustic signal transmission means 101 and the acoustic signal observation means 102 may transmit the acoustic signal to each of the right and left ear canals and/or pinnae and perform observation, to obtain two observation acoustic signals. The noise/device property removal means 201 may remove noise and device property, using the two observation acoustic signals observed in such a way.

As another method of noise/device property removal, for example, the noise/device property removal means 201 may average two or more observation acoustic signals obtained by performing an operation of observing the acoustic signal transmitted from the acoustic signal transmission means 101 by the acoustic signal observation means 102 a plurality of times. This method can reduce the influence of noise that occurs instantaneously.

Yet another method of noise/device property removal is a method of storing an average of observation acoustic signals observed from a plurality of persons beforehand and, upon authentication, subtracting the stored average from the observation acoustic signal observed from the user (first user) to be authenticated. The average of the observation acoustic signals observed from the plurality of persons is considered to contain common property not dependent on a specific person. Accordingly, noise and device property can be removed by subtracting such common property from the observation acoustic signal of the first user.

Figure 7:
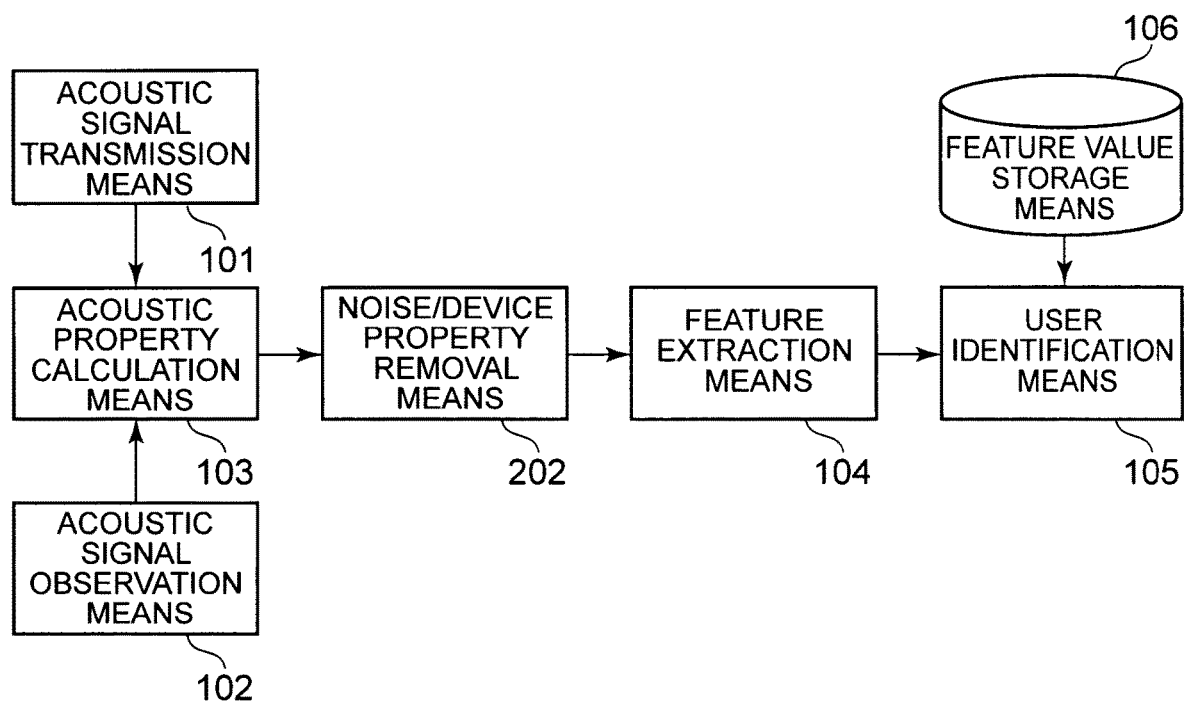
FIG. 7 is a block diagram depicting another example of the structure of the personal authentication device in Exemplary Embodiment 2.
Figure 8:
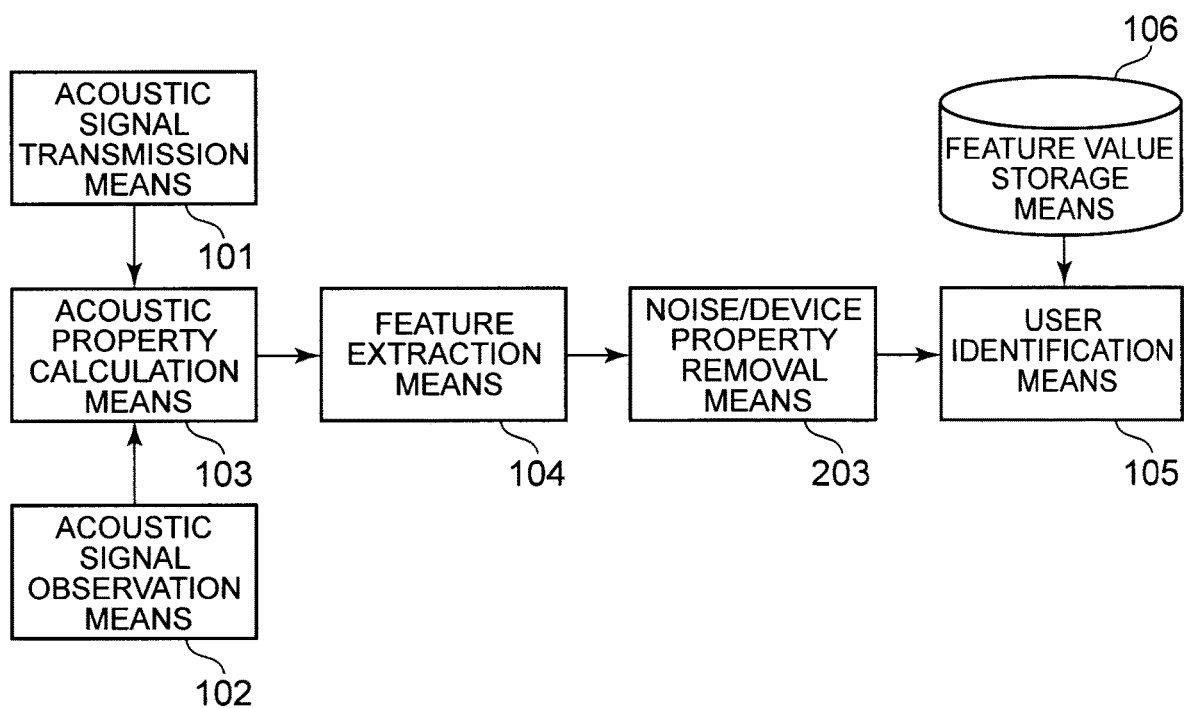
FIG. 8 is a block diagram depicting another example of the structure of the personal authentication device in Exemplary Embodiment 2.

FIGS. 7 and 8 are each a block diagram depicting another example of the structure of the personal authentication device in this exemplary embodiment. As depicted in FIGS. 7 and 8, the position of the noise/device property removal means is not limited to be subsequent to the acoustic signal observation means 102. As an example, the noise/device property removal means may be located subsequent to the acoustic property calculation means 103, as depicted in FIG. 7. As another example, the noise/device property removal means may be located subsequent to the feature extraction means 104, as depicted in FIG. 8. FIG. 7 depicts noise/device property removal means 202, as an example of the noise/device property removal means located subsequent to the acoustic property calculation means 103. FIG. 8 depicts noise/device property removal means 203, as an example of the noise/device property removal means located subsequent to the feature extraction means 104.

In these examples, the noise/device property removal means 202 removes noise and device property from the acoustic property calculated by the acoustic property calculation means 103, and the noise/device property removal means 203 removes noise and device property from the feature value calculated by the feature extraction means 104.

An example of the method of removing noise and device property from the acoustic property is a method of subtracting common acoustic property obtained from observation acoustic signals observed at two locations of the head of the user. Another example is a method of averaging acoustic property obtained from observation acoustic signals resulting from observation performed a plurality of times. Yet another example is a method of subtracting acoustic property obtained from an average of observation acoustic signals observed from a plurality of persons, from the acoustic property obtained from the observation acoustic signal observed from the user to be authenticated.

The method of removing noise and device property from the feature value may be the same as the method of removing noise and device property from the acoustic property, i.e. the method of subtraction or averaging (with "acoustic property" being replaced with "feature value"), or a method of measuring the standard deviation of the acoustic property and performing division.

Each of the noise/device property removal means 201, the noise/device property removal means 202, and the noise/device property removal means 203 may remove device property by subtracting, from the observation acoustic signal (or acoustic property or feature value obtained from the observation acoustic signal), an acoustic signal (or acoustic property or feature value obtained from the acoustic signal) obtained by propagation through only the earphone and the microphone without involving the head.

Exemplary Embodiment 2 is the same as Exemplary Embodiment 1 in other respects.

As described above, according to this exemplary embodiment, various noise such as ambient environmental noise, cardiac sound, respiratory sound, utterance, joint sound, and vibration and device property which is an individual device difference can be removed from the observation acoustic signal or its acoustic property or feature value. This enables more accurate personal authentication than in Exemplary Embodiment 1.

Exemplary Embodiment 3

Figure 9:
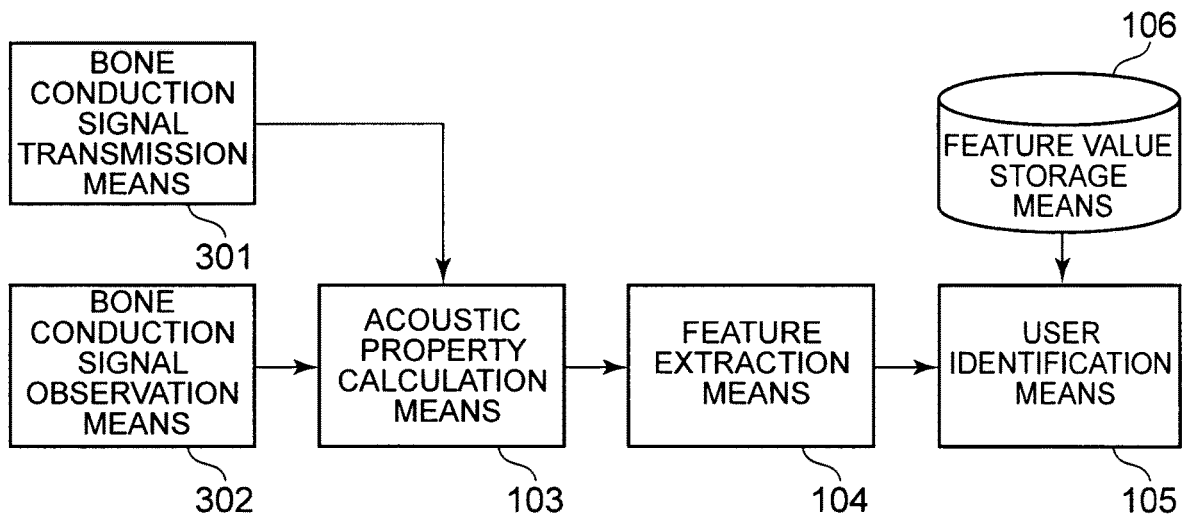
FIG. 9 is a block diagram depicting an example of the structure of a personal authentication device in Exemplary Embodiment 3.

Exemplary Embodiment 3 of the present invention is described below. FIG. 9 is a block diagram depicting an example of the structure of a personal authentication device in Exemplary Embodiment 3 of the present invention. The personal authentication device depicted in FIG. 9 has a structure in which the acoustic signal transmission means 101 and the acoustic signal observation means 102 in the structure of Exemplary Embodiment 1 depicted in FIG. 1 are replaced with bone conduction signal transmission means 301 and bone conduction signal observation means 302.

Sound typically propagates through air as a main medium, but can also propagate through bones as a medium. The propagation of sound through bones as a medium is called bone conduction. Bone conduction propagation property has individuality, too. Hence, an observation acoustic signal obtained as a result of bone conduction can be used for personal authentication.

The bone conduction signal transmission means 301 transmits a bone conduction signal which is an acoustic signal for bone conduction, from a part of the head as a transmission acoustic signal. The part of the head to which the bone conduction signal is transmitted is, for example, a region where a bone is formed in the head, and may be at least a part of a region to which an accessory or a device for producing an acoustic effect can be attached or brought close.

The bone conduction signal observation means 302 observes a bone conduction signal after the bone conduction signal transmitted from the bone conduction signal transmission means 301 propagates through the part of the head of the user, as an observation acoustic signal. The part of the head which is the propagation path of the bone conduction signal may be at least a part of the skull, teeth, brain, sense organ, and cavity therebetween constituting the head. The propagation path includes at least a bone.

The bone conduction signal observation means 302 may be realized by, for example, a bone conduction microphone. Here, the bone conduction signal observation means 302 may observe the bone conduction signal from a part different from the given part of the head to which the bone conduction signal transmission means 301 transmits the bone conduction signal. Exemplary Embodiment 3 is the same as Exemplary Embodiment 1 in other respects.

As described above, according to this exemplary embodiment, personal authentication can be performed by use of acoustic signal transmission property by bone conduction. This enables personal authentication to be performed without covering the user's auditory organ such as the ear.

Exemplary Embodiment 4

Figure 10:
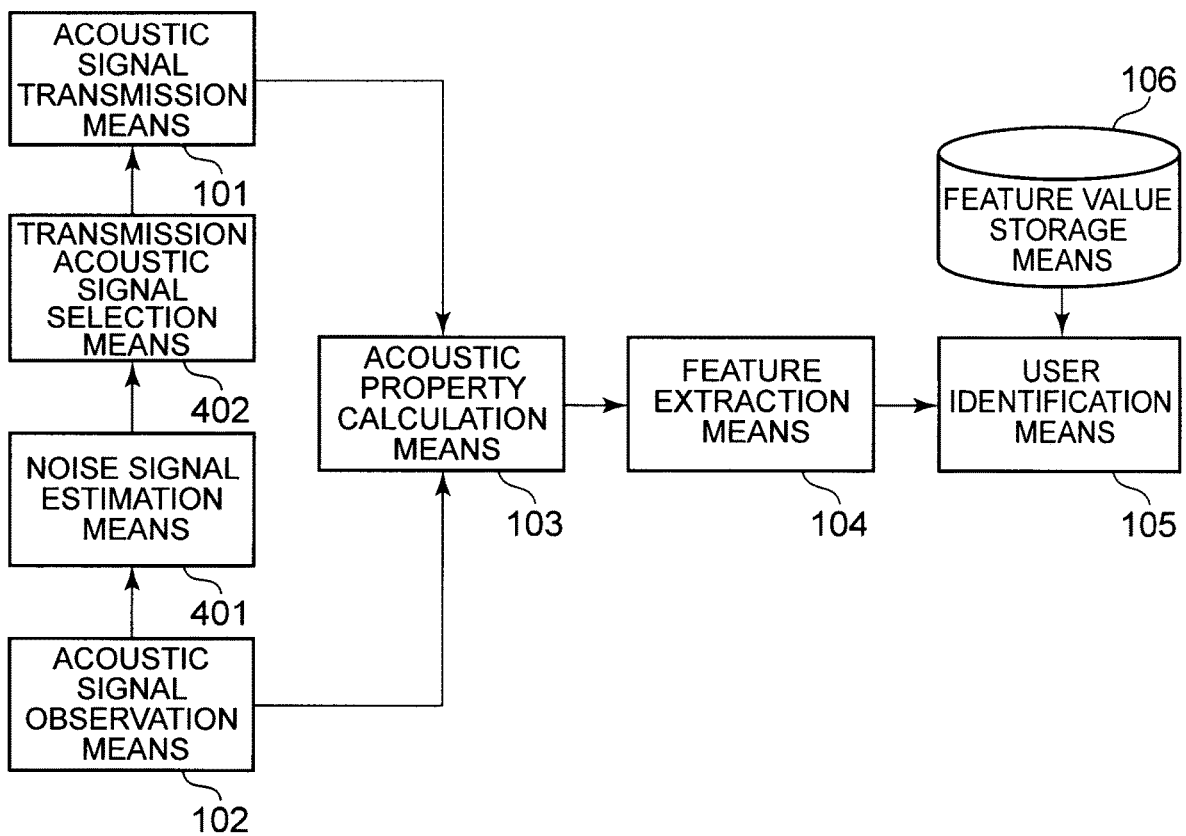
FIG. 10 is a block diagram depicting an example of the structure of a personal authentication device in Exemplary Embodiment 4.

Exemplary Embodiment 4 of the present invention is described below. FIG. 10 is a block diagram depicting an example of the structure of a personal authentication device in Exemplary Embodiment 4 of the present invention. The personal authentication device depicted in FIG. 10 has a structure in which noise signal estimation means 401 and transmission acoustic signal selection means 402 are added to the structure of Exemplary Embodiment 1 depicted in FIG. 1.

The noise signal estimation means 401 estimates a noise signal from an observation acoustic signal. For example, the noise signal estimation means 401 estimates a noise signal, from an observation acoustic signal observed at or near a part of the head of the user in a state where an acoustic signal for authentication is not transmitted.

The transmission acoustic signal selection means 402 selects an acoustic signal of a frequency band different from the frequency band of the estimated noise signal, as a transmission acoustic signal.

FIG. 11 is a flowchart depicting an example of the operation of the personal authentication device in this exemplary embodiment. The same operations as those in Exemplary Embodiment 1 are given the same reference signs, and their description is omitted. In the example depicted in FIG. 11, the personal authentication device observes an acoustic signal using the acoustic signal observation means 102, before transmitting an acoustic signal to the part of the head of the user (step S201).

Subsequently, the noise signal estimation means 401 estimates a noise signal using the observed acoustic signal (step S202).

Subsequently, the transmission acoustic signal selection means 402 selects a transmission acoustic signal, based on the estimated noise signal (step S203). The subsequent operations may be the same as those in Exemplary Embodiment 1.

According to this exemplary embodiment, the influence of noise such as ambient environmental noise can be avoided.

Exemplary Embodiment 5

Exemplary Embodiment 5 of the present invention is described below. The structure of this exemplary embodiment may be the same as that of Exemplary Embodiment 1, except that the acoustic signal transmission means 101 in this exemplary embodiment changes the transmission acoustic signal regularly or irregularly. An example of the irregular change is a method of, in the case of performing authentication randomly, changing the transmission acoustic signal each time authentication is performed. Another example is a method of, in the case of changing the number of times authentication is performed or the frequency at which authentication is performed depending on authentication reliability, changing the transmission acoustic signal each time authentication is performed. Yet another example is a method of, in the case of performing authentication each time the user makes some kind of service request, changing the transmission acoustic signal each time authentication is performed. Yet another example is a method of, in the case of performing authentication at timing of an interval of a service such as a change of music, changing the transmission acoustic signal each time authentication is performed.

In the case where the acoustic signal transmission means 101 transmits the same acoustic signal, the acoustic signal observation means 102 observes the same acoustic signal as long as the user and his or her position are unchanged. In this case, there is a possibility that a malicious person eavesdrops the observation acoustic signal and succeeds in impersonation by some means. To prevent such an act, it is preferable to change the transmission acoustic signal in the case where the state in which the user and his or her position are unchanged continues. In this way, even if the observation acoustic signal is eavesdropped for impersonation, in the case where a process of comparison with the transmission acoustic signal results in at least a predetermined difference in signal element between the two signals, the user to be authenticated can be rejected as an impostor.

Moreover, by separating the signal path until the acoustic signal transmission means 101 transmits the transmission acoustic signal and the signal path until the acoustic signal observation means 102 receives the transmission acoustic signal in the personal authentication device, the risk of simultaneous eavesdropping of two acoustic signals (transmission acoustic signal and observation acoustic signal) can be avoided.

Exemplary Embodiment 6

Exemplary Embodiment 6 of the present invention is described below. The structure of this exemplary embodiment may be the same as that of Exemplary Embodiment 1, except that the acoustic signal transmission means 101 in this exemplary embodiment uses musical sound as a transmission acoustic signal. This further lessens the psychological/physical burden on the user.

The acoustic signal transmission means 101 may transmit, as the transmission acoustic signal, the music on which another acoustic signal (such as white noise) is superimposed, for the purpose of improving the amplitude of a low-amplitude component in the musical sound or for the purpose of compensating for a low-power component of the frequency components in the musical sound. Further, in the case where a service using an acoustic signal itself, such as music distribution, transceiver, or telephone, is provided, the acoustic signal transmission means 101 may transmit the acoustic signal used for the service, as the transmission acoustic signal.

FIGS. 12(*a*) and 12(*b*) are explanatory diagrams depicting an example of a transmission acoustic signal obtained by superimposing, on an acoustic signal of music, another acoustic signal for the purpose of improving the amplitude of a low-amplitude component in the musical sound. FIG. 12(*a*) depicts the voice signal of the original music, with the horizontal axis representing time and the vertical axis representing the signal value. FIG. 12(*b*) depicts the transmission acoustic signal obtained by adding white noise to the original music, with the horizontal axis representing time and the vertical axis representing the signal value. As depicted in FIGS. 12(*a*) and 12(*b*), the amplitude of the low-amplitude component is improved by adding white noise or the like to the original music. Here, the absolute value of the signal value corresponds to the amplitude.

Figure 13A:
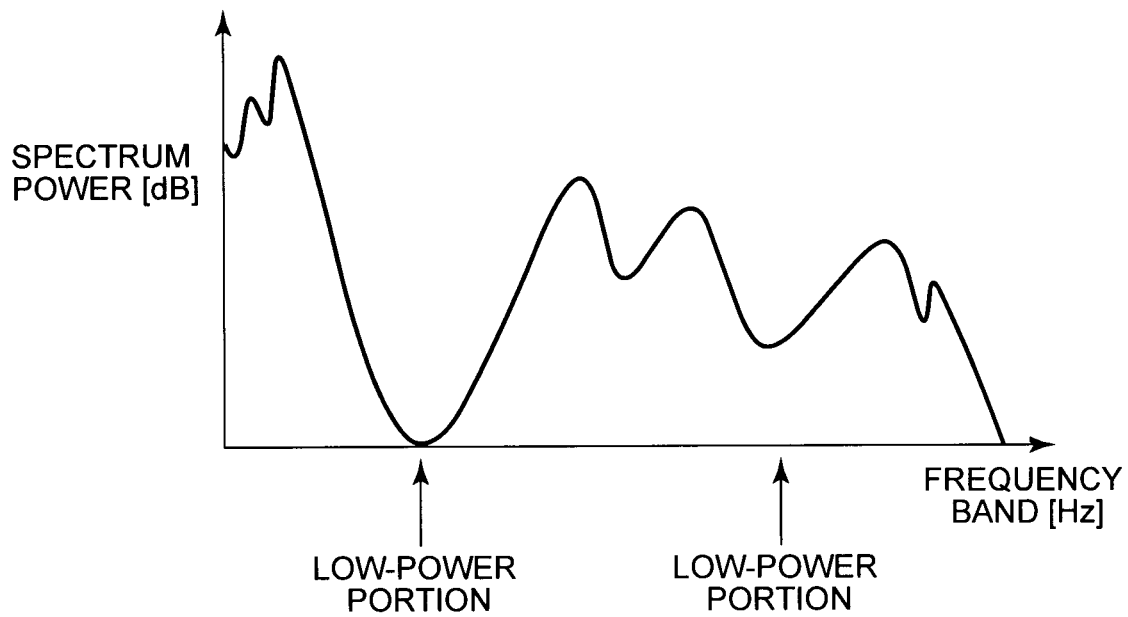
FIGS. 13(a) and 13(b) are explanatory diagrams depicting an example of superimposing, on musical sound, another acoustic signal.
Figure 13B:
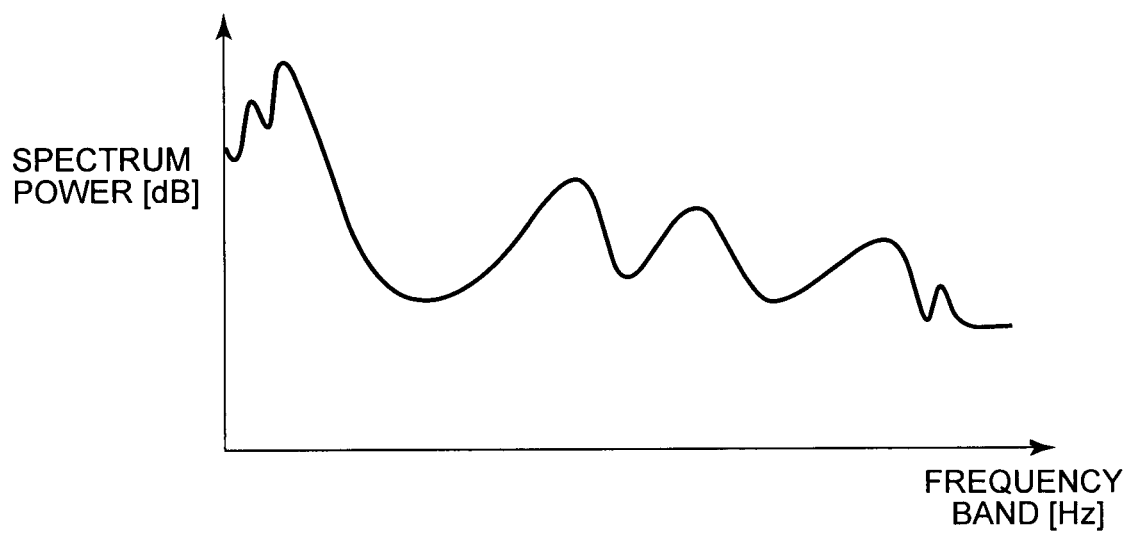
Figure 14:
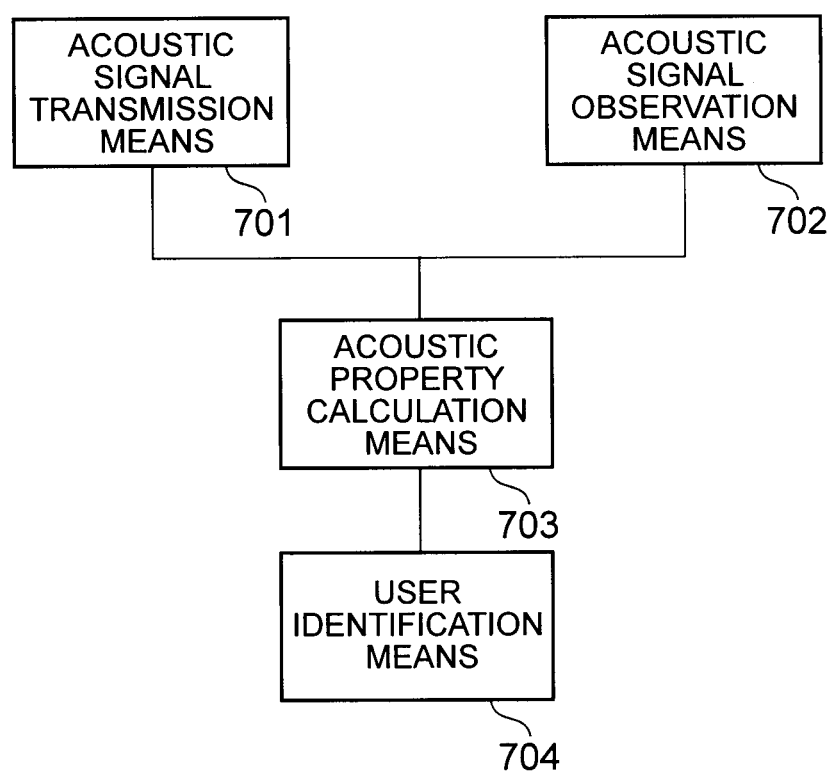
FIG. 14 is a block diagram depicting an overview of the present invention.

FIGS. 13(*a*) and 13(*b*) are explanatory diagrams depicting an example of a transmission acoustic signal obtained by superimposing, on an acoustic signal of music, another acoustic signal for the purpose of compensating for a low-power component of the frequency components in the musical sound. FIG. 13(*a*) depicts the spectrum power of the original music. FIG. 13(*b*) depicts the spectrum power of the transmission acoustic signal obtained by adding white noise to the original music. FIGS. 13(*a*) and 13(*b*) both depict a value obtained by Fourier transform, with the horizontal axis representing frequency and the vertical axis representing spectrum power in logarithmic axes. As depicted in FIGS. 13(*a*) and 13(*b*), the low-power portion is compensated for by adding white noise or the like to the original music.

The foregoing exemplary embodiments may be used in combination. Moreover, although the foregoing exemplary embodiments each describe an example where the personal authentication device operates alone, the personal authentication device may be used in combination with another device. As an example, a personalization system that provides a service different for each person based on a result of specifying a person using any of the personal authentication devices described above may be provided. The system may include, in addition to the personal authentication device, service provision means (not depicted) for providing a service different for each person based on a specification result output from the personal authentication device.

As another example, a content right management system that determines whether or not the user has a legitimate right based on a result of specifying a person using any of the personal authentication devices described above may be provided. The system may include, in addition to the personal authentication device, means for determining whether or not the user has a legitimate right to content based on a specification result output from the personal authentication device, and means for providing a service such as content only in the case where the user has a legitimate right as a result of the determination.

As yet another example, a voice communication control system that performs voice communication only for a specific person based on a result of specifying a person using any of the personal authentication devices described above may be provided. The system may include, in addition to the personal authentication device, means for controlling voice communication such as permitting only a designated person to perform voice communication based on a specification result output from the personal authentication device. There is a possibility that voice communication is eavesdropped unless it is, for example, encrypted. Even when the voice communication is encrypted, there is a possibility that the voice communication is eavesdropped through leakage, theft, or the like of the cipher. For example, by encrypting voice using acoustic property extracted for each person by the personal authentication device, voice communication that has low possibility of leakage or theft can be realized. Moreover, for example, voice communication by secret key/public key cryptography may be realized using, as a secret key, acoustic property extracted for each person by the personal authentication device. Communication provided by the system is not limited to voice communication, and may be, for example, data communication.

An overview of the present invention is described below. FIGS. 13(*a*) and 13(*b*) are block diagrams depicting an overview of a personal authentication device according to the present invention. The personal authentication device depicted in FIGS. 13(*a*) and 13(*b*) includes acoustic signal transmission means 701, acoustic signal observation means 702, acoustic property calculation means 703, and user identification means 704.

The acoustic signal transmission means 701 transmits a first acoustic signal to a part of the head of a user. For example, the acoustic signal transmission means 701 may be realized as an accessory or a device for producing an acoustic effect, which is attached to a region, or its vicinity, where a cavity or a bone is formed in the head of the user, in order to transmit the first acoustic signal.

The acoustic signal observation means 702 observes a second acoustic signal which is an acoustic signal after the first acoustic signal propagates through the part of the head. The part of the head as the propagation path of the acoustic signal may include at least a part of the skull, brain, sense organ, and cavity therebetween constituting the head.

The acoustic property calculation means 703 calculates an acoustic property from the first acoustic signal and the second acoustic signal.

The user identification means 704 identifies the user, based on the calculated acoustic property or a feature value extracted from the acoustic property and relating to the user.

With such a structure, personal authentication can be performed without a special action by the user for authentication. Personal authentication that lessens the psychological and/or physical burden on the user to be authenticated can thus be realized.

Although not depicted, the personal authentication device may further include feature extraction means for extracting a feature value relating to the user from the acoustic property. In this case, the user identification means may identify the user, based on the feature value extracted by the feature extraction means and relating to the user.

The foregoing exemplary embodiments can be described as, but not limited to, the following supplementary notes.

(Supplementary note 1) A personal authentication device including: acoustic signal transmission means for transmitting a first acoustic signal to a part of a head of a user; acoustic signal observation means for observing a second acoustic signal which is an acoustic signal after the first acoustic signal propagates through the part of the head; acoustic property calculation means for calculating an acoustic property from the first acoustic signal and the second acoustic signal; and user identification means for identifying the user, based on the acoustic property or a feature value extracted from the acoustic property and relating to the user.

(Supplementary note 2) The personal authentication device according to supplementary note 1, including storage means for storing beforehand, for at least one person, an acoustic property at a time of propagation of an acoustic signal through a predetermined part of a head of the person or a feature value extracted from the acoustic property, wherein the user identification means identifies the user, by comparing the acoustic property calculated from the second acoustic signal with the acoustic property stored in the storage means or comparing the feature value extracted from the acoustic property calculated from the second acoustic signal with the feature value stored in the storage means.

(Supplementary note 3) The personal authentication device according to supplementary note 1 or 2, wherein the part of the head which is a propagation path of the first acoustic signal includes at least one ear canal and/or pinna.

(Supplementary note 4) The personal authentication device according to any one of supplementary notes 1 to 3, wherein the acoustic signal transmission means is realized by an earphone, a headphone, or a receiver portion of a telephone, and wherein the acoustic signal observation means is realized by a microphone mounted on the earphone, the headphone, or the receiver portion of the telephone.

(Supplementary note 5) The personal authentication device according to any one of supplementary notes 1 to 4, including removal means for removing ambient noise and/or a device property from the second acoustic signal, based on acoustic signals observed at two locations of the head of the user, acoustic signals observed from the same user a plurality of times, or acoustic signals observed from a plurality of persons.

Here, the removal means may, using acoustic signals observed as a result of transmitting the acoustic signal to each of the right and left ear canals and/or pinnae, remove ambient noise and/or a device property from at least one of the observed acoustic signals.

(Supplementary note 6) The personal authentication device according to any one of supplementary notes 1 to 5, wherein the acoustic signal transmission means transmits an acoustic signal for bone conduction, as the first acoustic signal, and the acoustic signal observation means observes the second acoustic signal after the first acoustic signal propagates through the part of the head by bone conduction, as the second acoustic signal.

Here, the acoustic signal observation means may be realized by a bone conduction microphone. Moreover, the acoustic signal observation means may observe the second acoustic signal from a part different from the part of the head to which the acoustic signal transmission means transmits the first acoustic signal.

(Supplementary note 7) The personal authentication device according to any one of supplementary notes 1 to 6, including noise estimation means for estimating a noise signal, based on an acoustic signal observed by the acoustic signal observation means, wherein the acoustic signal transmission means transmits an acoustic signal of a frequency band different from a frequency band of the noise signal estimated by the noise estimation means, as the first acoustic signal from next time.

(Supplementary note 8) The personal authentication device according to any one of supplementary notes 1 to 7, wherein the acoustic signal transmission means changes the first acoustic signal regularly or irregularly.

(Supplementary note 9) The personal authentication device according to any one of supplementary notes 1 to 8, wherein the first acoustic signal is musical sound.

(Supplementary note 10) The personal authentication device according supplementary note 9, wherein the acoustic signal transmission means transmits, as the first acoustic signal: an acoustic signal obtained by superimposing, on an acoustic signal of music, another acoustic signal for the purpose of improving the amplitude of a low-amplitude component in the musical sound; or an acoustic signal obtained by superimposing, on an acoustic signal of music, another acoustic signal for the purpose of compensating for a low-power component of the frequency components in the musical sound.

(Supplementary note 11) A personal authentication method including: transmitting a first acoustic signal to a part of a head of a user; observing a second acoustic signal which is an acoustic signal after the first acoustic signal propagates through the part of the head; calculating an acoustic property from the first acoustic signal and the second acoustic signal; and identifying the user, based on the acoustic property or a feature value extracted from the acoustic property and relating to the user.

(Supplementary note 12) The personal authentication method according to supplementary note 11, wherein the user is identified by comparing the acoustic property or feature value acquired from the second acoustic signal with an acoustic property or feature value stored in storage means for storing beforehand, for at least one person, an acoustic property at the time of propagation of an acoustic signal through a predetermined part of the head or a feature value extracted from the acoustic property.

(Supplementary note 13) A personal authentication program for causing a computer to execute: a process of calculating an acoustic property, from a first acoustic signal transmitted to a part of a head of a user and a second acoustic signal which is an acoustic signal after the first acoustic signal propagates through the part of the head; and a process of identifying the user, based on the acoustic property or a feature value extracted from the acoustic property and relating to the user.

(Supplementary note 14) The personal authentication program according to supplementary note 13, causing the computer to, in the user identification process, identify the user by comparing the acoustic property or feature value acquired from the second acoustic signal with an acoustic property or feature value stored in storage means for storing beforehand, for at least one person, an acoustic property at the time of propagation of an acoustic signal through a predetermined part of the head or a feature value extracted from the acoustic property.

(Supplementary note 15) A personalization system including service provision means for providing a service different for each person based on a user identification result by the personal authentication device according to any one of supplementary notes 1 to 10.

(Supplementary note 16) A content right management system including determination means for determining whether or not a user has a legitimate right to content subjected to management, based on a user identification result by the personal authentication device according to any one of supplementary notes 1 to 10.

(Supplementary note 17) A communication control system including control means for controlling voice communication or data communication based on a user identification result by the personal authentication device according to any one of supplementary notes 1 to 10.

Although the present invention has been described with reference to the exemplary embodiments and examples, the present invention is not limited to the foregoing exemplary embodiments and examples. Various changes understandable by those skilled in the art can be made to the structures and details of the present invention within the scope of the present invention.

INDUSTRIAL APPLICABILITY

The present invention is suitable for use in, for example, a personal authentication device, a personal authentication method, or a personal authentication program for authenticating a person using an audio device. The present invention is also applicable to a personalization system, a content right management system, a communication control system, or the like using such a personal authentication device, personal authentication method, or personal authentication program.

REFERENCE SIGNS LIST

11 PC
12 sound processor
13 microphone amplifier
14 earphone
15 microphone
16 user
101 acoustic signal transmission means
102 acoustic signal observation means
103 acoustic property calculation means
104 feature extraction means
105 user identification means
106 feature value storage means
201, 202, 203 noise/device property removal means
301 bone conduction signal transmission means
302 bone conduction signal observation means
401 noise signal estimation means
402 transmission acoustic signal selection means
701 acoustic signal transmission means
702 acoustic signal observation means
703 acoustic property calculation means
704 user identification means

The invention claimed is:

1. A personal authentication device comprising:
an acoustic signal transmission unit which transmits a first acoustic signal to a part of a head of a user;
an acoustic signal observation unit which observes a second acoustic signal which is an acoustic signal after the first acoustic signal propagates through the part of the head;
an acoustic property calculation unit implemented at least by a hardware including a processor and which calculates an acoustic property from the first acoustic signal and the second acoustic signal; and
a user identification unit implemented at least by the hardware and which identifies the user, based on the acoustic property or a feature value extracted from the acoustic property and relating to the user,
wherein the acoustic signal transmission unit is further configured to transmit a transmission acoustic signal used for removing ambient noise and/or a device property not dependent on the positional difference in the head to a right ear canal and a left ear canal of the user simultaneously, or pinnae of the user,
the device further comprising a removal unit implemented at least by the hardware and which removes the ambient noise and/or the device property from the second acoustic signal, by performing a calculation using at least two acoustic signals, based on the transmission acoustic signal, observed at two locations of the head.

2. The personal authentication device according to claim 1, comprising
a storage unit which stores beforehand, for at least one person, an acoustic property at a time of propagation of an acoustic signal through a predetermined part of a head of the person or a feature value extracted from the acoustic property,
wherein the user identification unit identifies the user, by comparing the acoustic property calculated from the second acoustic signal with the acoustic property stored in the storage unit or comparing the feature value extracted from the acoustic property calculated from the second acoustic signal with the feature value stored in the storage unit.

3. The personal authentication device according to claim 1, wherein the acoustic signal transmission unit is realized by an earphone, a headphone, or a receiver portion of a telephone, and wherein the acoustic signal observation unit is realized by a microphone mounted on the earphone, the headphone, or the receiver portion of the telephone.

4. The personal authentication device according to claim 1, wherein
the removal unit removes the ambient noise and/or the device property from the second acoustic signal, based on acoustic signals observed from a plurality of persons.

5. The personal authentication device according to claim 1, wherein the acoustic signal transmission unit transmits an acoustic signal for bone conduction, as the first acoustic signal, and
the acoustic signal observation unit observes an acoustic signal after the first acoustic signal propagates through the part of the head by bone conduction, as the second acoustic signal.

6. The personal authentication device according to claim 1, comprising
a noise estimation unit implemented at least by the hardware and which estimates a noise signal, based on an acoustic signal observed by the acoustic signal observation unit,
wherein the acoustic signal transmission unit transmits an acoustic signal of a frequency band different from a frequency band of the noise signal estimated by the noise estimation unit, as the first acoustic signal from next time.

7. The personal authentication device according to claim 1, wherein the acoustic signal transmission unit changes the first acoustic signal regularly or irregularly.

8. The personal authentication device according to claim 1, wherein
the acoustic signal transmission unit transmits acoustic signals a plurality of times; and
the removal unit averages two or more observed acoustic signals and removes the ambient noise and/or the device property from the second acoustic signal using an average value of the observed acoustic signals.

9. A personal authentication method comprising:
transmitting a first acoustic signal to a part of a head of a user;
observing a second acoustic signal which is an acoustic signal after the first acoustic signal propagates through the part of the head;
calculating by an information-processing device, an acoustic property from the first acoustic signal and the second acoustic signal;
identifying the user, by the information-processing device, based on the acoustic property or a feature value extracted from the acoustic property and relating to the user;
transmitting a transmission acoustic signal used for removing ambient noise and/or a device property not dependent on the positional difference in the head to a right ear canal and a left ear canal of the user, or pinnae of the user simultaneously; and
removing the ambient noise and/or the device property from the second acoustic signal, on the basis of at least two acoustic signals, based on the transmission acoustic signal, observed at two locations of the head.

10. The personal authentication method according to claim 9, wherein
transmitting acoustic signals a plurality of times; and
averaging two or more observed acoustic signals and removing the ambient noise and/or the device property from the second acoustic signal using an average value of the observed acoustic signals.

11. A non-transitory computer readable recording medium in which a personal authentication program is recorded, the personal authentication program for causing a computer to execute:
a process of calculating an acoustic property, from a first acoustic signal transmitted to a part of a head of a user and a second acoustic signal which is an acoustic signal after the first acoustic signal propagates through the part of the head;
a process of identifying the user, based on the acoustic property or a feature value extracted from the acoustic property and relating to the user;
a process of transmitting a transmission acoustic signal used for removing ambient noise and/or a device property not dependent on the positional difference in the head to a right ear canal and a left ear canal of the user, or pinnae of the user simultaneously; and
a process of removing the ambient noise and/or the device property from the second acoustic signal, on the basis of at least two acoustic signals, based on the transmission acoustic signal, observed at two locations of the head.

* * * * *